US012357272B2

(12) United States Patent
Chen et al.

(10) Patent No.: US 12,357,272 B2
(45) Date of Patent: Jul. 15, 2025

(54) DETECTION MODE CONTROL CIRCUIT

(71) Applicant: Wuxi Hisky Medical Technologies Co., Ltd., Wuxi (CN)

(72) Inventors: Gang Chen, Wuxi (CN); Jianhua Jiao, Wuxi (CN); Jinhua Shao, Wuxi (CN); Jin Sun, Wuxi (CN); Houli Duan, Wuxi (CN)

(73) Assignee: Wuxi Hisky Medical Technologies Co., Ltd., Wuxi (CN)

( * ) Notice: Subject to any disclaimer, the term of this patent is extended or adjusted under 35 U.S.C. 154(b) by 669 days.

(21) Appl. No.: 17/575,579

(22) Filed: Jan. 13, 2022

(65) Prior Publication Data

US 2022/0133271 A1    May 5, 2022

Related U.S. Application Data

(63) Continuation of application No. PCT/CN2020/090557, filed on May 15, 2020.

(30) Foreign Application Priority Data

Jul. 15, 2019    (CN) .......................... 201910636228.2

(51) Int. Cl.
*A61B 8/00*    (2006.01)
(52) U.S. Cl.
CPC .......... *A61B 8/4455* (2013.01); *A61B 8/4494* (2013.01)
(58) Field of Classification Search
CPC ....... A61B 8/4455; A61B 8/4494; A61B 8/44; A61B 8/485; A61B 8/54; A61B 8/085; G05B 19/04
See application file for complete search history.

(56) References Cited

U.S. PATENT DOCUMENTS

2007/0178534 A1    8/2007 Murphy
2008/0071172 A1    3/2008 Bruck
(Continued)

FOREIGN PATENT DOCUMENTS

CN    1054891 A    10/1991
CN    2219001 Y    1/1996
(Continued)

OTHER PUBLICATIONS

First Office Action of the parallel application JP2022-502501.
(Continued)

*Primary Examiner* — Michael J Carey
*Assistant Examiner* — Zainab Mohammed Aldarraji
(74) *Attorney, Agent, or Firm* — J.C. PATENTS

(57) ABSTRACT

A detection mode control circuit, including a morphological detection module (100) connected to a morphological detection probe (500), where the morphological detection module (100) is configured to generate a morphological detection control signal according to a user instruction or a system setting; further including an elasticity detection module (200) connected to a switch module (300) and configured to generate an elasticity detection control signal and a second control signal according to the user instruction or the system setting; where the switch module (300) is connected to a compound probe (600) and configured to receive the morphological detection control signal, the elasticity detection control signal and the second control signal, and control the compound probe (600) to perform morphological detection according to the second control signal or control the compound probe (600) to perform elasticity detection according to the second control signal.

10 Claims, 1 Drawing Sheet

(56) References Cited

U.S. PATENT DOCUMENTS

| | | |
|---|---|---|
| 2009/0112099 A1 | 4/2009 | Kurokawa |
| 2009/0318779 A1 | 12/2009 | Tran |
| 2012/0071710 A1 | 3/2012 | Gazdzinski |
| 2014/0073884 A1 | 3/2014 | Yu |
| 2016/0030003 A1 | 2/2016 | Liu |
| 2016/0143621 A1 | 5/2016 | Parthasarathy |
| 2018/0310922 A1 | 11/2018 | Pelissier |
| 2019/0000430 A1 | 1/2019 | Tehrani |

FOREIGN PATENT DOCUMENTS

| | | | |
|---|---|---|---|
| CN | 101249005 A | | 8/2008 |
| CN | 101455575 A | | 6/2009 |
| CN | 201299585 Y | | 9/2009 |
| CN | 101810493 A | | 8/2010 |
| CN | 102813531 A | | 12/2012 |
| CN | 202821626 U | | 3/2013 |
| CN | 103300885 A | | 9/2013 |
| CN | 103784166 A | | 5/2014 |
| CN | 103917889 A | | 7/2014 |
| CN | 104107067 A | | 10/2014 |
| CN | 104302232 A | | 1/2015 |
| CN | 104856729 A | * 8/2015 | ............ A61B 8/085 |
| CN | 204789489 U | | 11/2015 |
| CN | 105395218 A | | 3/2016 |
| CN | 106108947 A | | 11/2016 |
| CN | 107198543 A | | 9/2017 |
| CN | 108056791 A | | 5/2018 |
| CN | 108095763 A | | 6/2018 |
| CN | 108095765 A | | 6/2018 |
| CN | 208573753 U | | 3/2019 |
| CN | 110297436 A | | 10/2019 |
| CN | 210222508 U | | 3/2020 |
| JP | 2014073411 A | | 4/2014 |
| JP | 2014518124 A | | 7/2014 |
| JP | 2016067392 A | | 5/2016 |
| TW | 447215 B | | 7/2001 |

OTHER PUBLICATIONS

The first Office Action of the priority application CN201910636228.2.
Extended European Search Report of the parallel application EP20839570.7.
First Office Action of the parallel application RU2022103636.
Third Office Action of the parallel application RU2022103636.
"Measurement of the temperature dependence of Young's modulus of cartilage by phase-sensitive optical coherence elastography", Quantum Electronics, 44(8) 751-756 (2014).
International Search Report of PCT/CN2020/090557.
Notice of Allowance of the priority application CN201910636228.2.

* cited by examiner

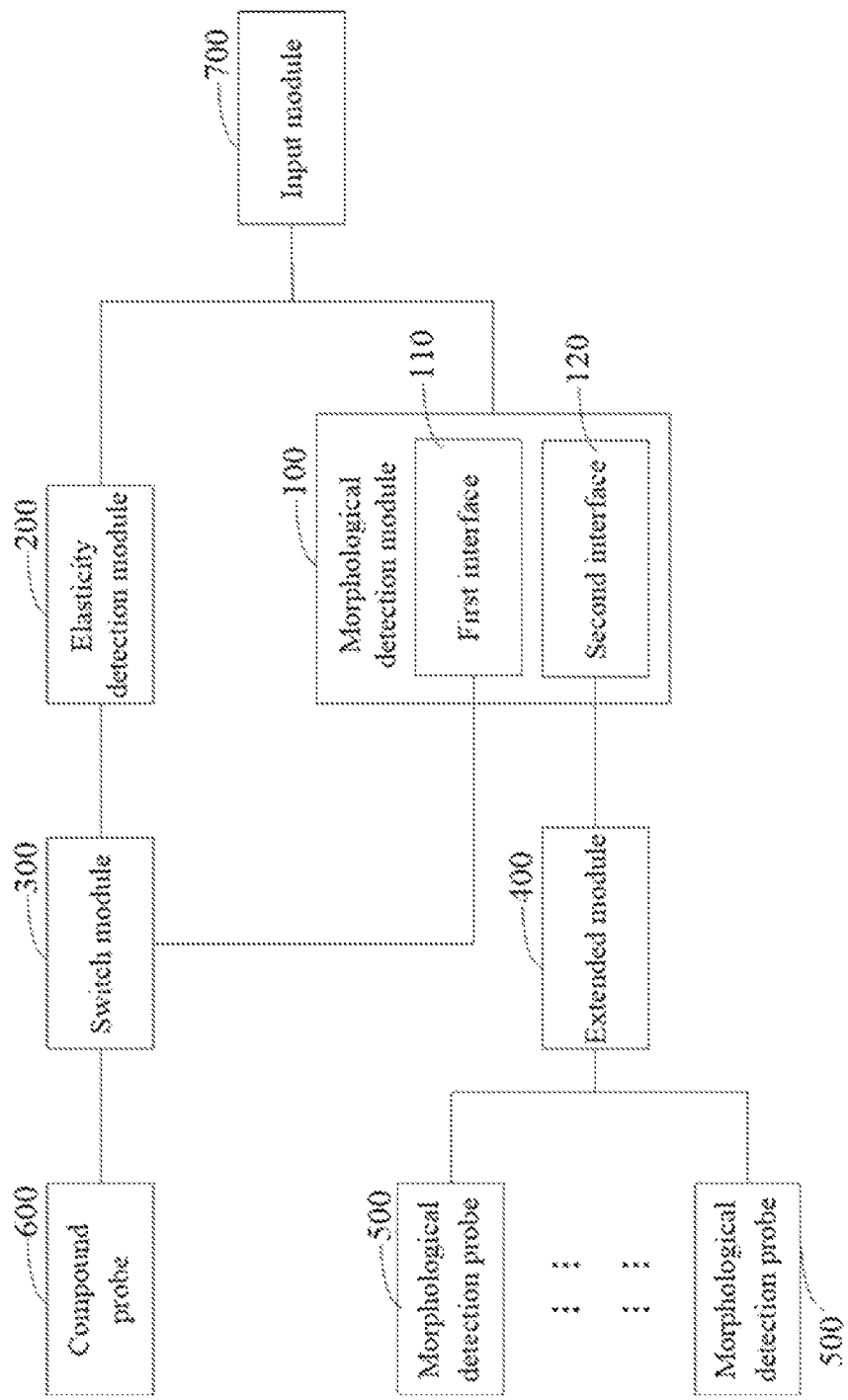

DETECTION MODE CONTROL CIRCUIT

CROSS-REFERENCE TO RELATED APPLICATIONS

This application is a continuation of International Application No. PCT/CN2020/090557, filed on May 15, 2020, which claims priority to Chinese Patent Application No. 201910636228.2, filed on Jul. 15, 2019. Both of the aforementioned applications are hereby incorporated by reference in their entireties.

TECHNICAL FIELD

The present disclosure relates to the technical field of medical detection device and, in particular, to a detection mode control circuit.

BACKGROUND

Progression of various chronic liver diseases such as viral hepatitis (hepatitis A, hepatitis B, hepatitis C, etc.) will be accompanied by liver fibrosis, and a process of the liver fibrosis will be accompanied by an increase of liver elasticity. Therefore, liver elasticity information is a parameter that can be used to diagnose a degree of fibrosis of liver tissue. Transient elastography technology is a technology for quantitatively detecting elastic modulus of tissues, and this technology transmits low-frequency shear waves to a liver through a body surface, tracks propagation of the shear waves in tissues, and then can accurately and quantitatively calculate the elastic modulus of the tissues. A detection process of the elastic modulus of the tissues is referred to as E-ultrasonic detection for short.

At present, a better solution is to carry out histomorphological detection, such as B-mode ultrasonography, computed tomography (CT), etc., so as to accurately locate an area to be detected and eliminate interference of ribs, connective tissues, blood vessels, etc., thereby improving accuracy of the E-ultrasonic detection.

However, there is a disadvantage in the above solution. When appropriate diagnosis positions and angles are selected through morphological detection, an E-ultrasonic probe needs to be replaced. Since it cannot be guaranteed that positions corresponding to probes before and after replacement are completely consistent in a process of replacing the probe, and offset of a detection position will lead to deviation of diagnostic data, the accuracy of the E-ultrasonic detection is then affected.

SUMMARY

Based on this, it is necessary to provide a detection mode control circuit to solve the problem that deviation of a detection position leads to deviation of diagnosis data which causes misdiagnosis.

A detection mode control circuit includes: a morphological detection module, an elasticity detection module and a switch module, where the morphological detection module is connected to the switch module and configured to generate a morphological detection control signal according to a user instruction or a system setting and transmit the morphological detection control signal to the switch module; the elasticity detection module is connected to the switch module and configured to generate an elasticity detection control signal and a second control signal according to the user instruction or the system setting, and transmit the elasticity detection control signal and the second control signal to the switch module; and the switch module is connected to a compound probe and configured to receive the morphological detection control signal, the elasticity detection control signal, and the second control signal, and transmit, according to the second control signal, the morphological detection control signal to the compound probe to perform morphological detection, or transmit, according to the second control signal, the elasticity detection control signal to the compound probe to perform elasticity detection.

In one of embodiments, the morphological detection module includes a first interface and a second interface, where the morphological detection module is connected to the switch module through the first interface, and the morphological detection module is connected to a morphological detection probe through the second interface; the morphological detection module is configured to generate the morphological detection control signal and a first control signal according to the user instruction or the system setting; and the first control signal controls the first interface and the second interface to turn on or off, and transmits the morphological detection control signal to the switch module through the first interface, or transmits the morphological detection control signal to the morphological detection probe through the second interface to perform the morphological detection.

In one of the embodiments, the morphological detection module includes a plurality of second interfaces.

In one of the embodiments, the detection mode control circuit further includes an extended module, where the extended module is connected to the morphological detection module through the second interface, and the extended module includes a plurality of output interfaces which are respectively connected to a morphological detection probe.

In one of the embodiments, the morphological detection module is further configured to generate a third control signal according to the user instruction or the system setting, and transmit the third control signal to the extended module; and the extended module controls the plurality of output interfaces to turn on or off according to the third control signal.

In one of the embodiments, the third control signal controls each of the output interfaces of the extended module to turn on or off.

In one of the embodiments, the switch module is connected to M array elements in the compound probe, and is configured to control the M array elements to conduct with the elasticity detection module or the morphological detection module; and there are N array elements in the compound probe; where M is less than or equal to N, and M and N are positive integers.

In one of the embodiments, the switch module includes a relay array.

In one of the embodiments, the detection mode control circuit further includes an input module; where the input module is respectively connected to the morphological detection module and the elasticity detection module, and is configured to acquire the user instruction or store system setting information.

In one of the embodiments, the input module is configured to obtain the user instruction after processing according to user input information.

The detection mode control circuit provided by an embodiment of the present disclosure includes a morphological detection module, an elasticity detection module and a switch module. The morphological detection module generates a morphological detection control signal according to a user instruction or a system setting, and transmits the morphological detection control signal to the switch module. The elasticity detection module generates an elasticity detection control signal and a second control signal according to the user instruction or the system setting, and transmits them to the switch module. The switch module selectively transmits the morphological detection control signal or the elasticity detection control signal to a compound probe according to control of the second control signal, and controls the compound probe to perform morphological detection or elasticity detection. Through the detection mode control circuit, the embodiment of the present disclosure controls the compound probe to perform morphological detection and elasticity detection, and use of the compound probe for detection enables an elasticity detection position to be more accurate, and further enables diagnosis data to be more accurate.

BRIEF DESCRIPTION OF DRAWINGS

FIG. 1 is a schematic structural diagram of a detection mode control circuit provided by an embodiment of the present disclosure.

Reference numbers: 100 represents a morphological detection module; 110 represents a first interface; 120 represents a second interface; 200 represents an elasticity detection module; 300 represents a switch module; 400 represents an extended module; 500 represents a morphological detection probe; 600 represents a compound probe; and 700 represents an input module.

DESCRIPTION OF EMBODIMENTS

In order to make a purpose, a technical solution, and an advantage of the present disclosure clearer, the present disclosure will be further described in detail below with reference to the drawings and embodiments. It should be understood that the specific embodiments described here are only used to explain the present disclosure, and are not used to limit the present disclosure.

An embodiment of the present disclosure discloses a mode detection control circuit, where a morphological detection module is configured to generate a morphological detection control signal according to a user instruction or a system setting and transmit the morphological detection control signal to a switch module. An elasticity detection module generates an elasticity detection control signal and a second control signal according to the user instruction or the system setting. The second control signal controls the switch module to transmit the morphological detection control signal or the elasticity detection control signal to a compound probe to perform morphological detection or elasticity detection.

Please refer to FIG. 1, where FIG. 1 is a schematic structural diagram of a detection mode control circuit provided by an embodiment of the present disclosure.

As shown in FIG. 1, a detection mode control circuit includes: a morphological detection module 100, an elasticity detection module 200 and a switch module 300, where the morphological detection module 100 is connected to the switch module 300, and the morphological detection module 100 is configured to generate a morphological detection control signal according to a user instruction or a system setting and transmit the morphological detection control signal to the switch module 300; the elasticity detection module 200 is connected to the switch module 300 and configured to generate an elasticity detection control signal and a second control signal according to the user instruction or the system setting, and transmit the elasticity detection control signal and the second control signal to the switch module 300; the switch module 300 is connected to a compound probe 600 and configured to receive the morphological detection control signal, the elasticity detection control signal, and the second control signal, and transmit, according to the second control signal, the morphological detection control signal to the compound probe 600 to perform morphological detection, or transmit, according to the second control signal, the elasticity detection control signal to the compound probe 600 to perform elasticity detection.

In one of embodiments, the morphological detection module 100 includes a first interface 110 and a second interface 120, where the morphological detection module 100 is connected to the switch module 300 through the first interface 110, and the morphological detection module 100 is connected to a morphological detection probe 500 through the second interface 120; the morphological detection module 100 is configured to generate a morphological detection control signal and a first control signal according to the user instruction or the system setting; the first control signal controls the first interface 110 and the second interface 120 to turn on or off, and transmits the morphological detection control signal to the switch module 300 through the first interface 110 or transmits the morphological detection control signal to the morphological detection probe 500 through the second interface 120 to perform morphological detection.

Specifically, when a user needs to use the morphological detection probe 500 to perform morphological detection, the morphological detection module 100 generates the morphological detection control signal and the first control signal according to the user instructions or the system setting. Where the user instruction may be a control instruction received from the user via an upper computer, or a control instruction sent from a network side, etc. The system setting may be a control instruction stored in advance for the system. The morphological detection includes: B-mode ultrasonography, A-mode ultrasonography, M-mode ultrasonography, CT, and MRI, etc. Preferably, the morphological detection may be a B-mode ultrasonography detection; and the morphological detection probe may be a B-mode ultrasonography probe. The first control signal includes: an on or off signal of the first interface 110 and an on or off signal of the second interface 120. When the morphological detection probe is used, the first control signal controls the first interface 110 to turn off and the second interface 120 to turn on, i.e., the morphological detection module 100 transmits the morphological detection control signal to the morphological detection probe 500 through the second interface 120 to perform morphological detection. After detecting and obtaining a morphological detection echo signal, the morphological detection probe 500 transmits the morphological detection echo signal to the morphological detection module 100 through the second interface 120 for processing. When the user needs to use the compound probe 600 to position with morphological detection first and then perform elasticity detection on a determined position, the morphological detection module 100 receives input information from the user and generates the morphological detection control signal and the first control signal according to the input information from the user. The first control signal controls the first interface 110 to turn on and the second interface 120 to turn off, i.e., the morphological detection module 100 transmits the morphological detection control signal to the switch module 300 through the first interface 110. The elasticity detection module 200 receives input information from the user, generates the elasticity detection control signal, a motor drive signal, and the second control signal according to the input information from the user, and transmits the elasticity detection control signal, the motor drive signal, and the second control signal to the switch module 300. The elasticity detection includes: an E-ultrasonic detection, etc. The switch module 300 receives the morphological detection control signal, the elasticity detection control signal, the motor drive signal, and the second control signal. When a morphological detection position is needed, the second control signal controls the switch module 300 to enable the morphological detection module 100 to conduct with the compound probe 600, i.e., the morphological detection control signal is transmitted to the compound probe 600 to perform morphological detection. After the compound probe 600 performs the morphological detection to obtain a morphological detection echo signal, the morphological detection echo signal is transmitted to the morphological detection module 100 through the first interface 110 for processing. When morphological detection is needed, the second control signal controls the switch module 300 to enable the elasticity detection module 200 to conduct with the compound probe 600, i.e., to transmit the elasticity detection control signal and the motor drive signal to the compound probe 600 to drive the motor to vibrate to generate and emit low-frequency shear waves, to generate and emit ultrasonic waves to track the low-frequency shear waves, so as to perform elasticity detection, and then to transmit the elasticity detection echo signal to the elasticity detection module 200 for processing after the compound probe 600 performs the elasticity detection to obtain the elasticity detection echo signal. More specifically, only one of the first interface 110 and the second interface 120 is in an on state and the other is in an off state at one time. That is, when the morphological detection probe 500 is used for morphological detection, the compound probe 600 cannot perform morphological detection; and when the compound probe 600 is used for morphological detection, the morphological detection probe 500 cannot perform morphological detection.

In one of the embodiments, the morphological detection module 100 includes a plurality of second interfaces 120, i.e., the morphological detection module may be connected to a plurality of morphological detection probes 500 through the plurality of second interfaces 120.

Preferably, the detection mode control circuit further includes an extended module 400, where the extended module 400 is connected to the morphological detection module 100 through the second interface 120, and the extended module 400 includes a plurality of output interfaces, the plurality of output interfaces being respectively connected to a morphological detection probe 500.

Specifically, the morphological detection module 100 is further configured to generate a third control signal according to the user instruction or the system setting, and transmit the third control signal to the extended module 400; and the extended module 400 controls the plurality of output interfaces to turn on or off according to the third control signal. When the user needs to use the morphological detection probe 500 to perform morphological detection, the morphological detection module 100 transmits the morphological detection control signal to the extended module 400 through the second interface 120, and the extended module 400 controls each output interface to turn on or off according to the third control signal. The morphological detection control signal is transmitted to the morphological detection probe 500 corresponding to an on output interface through the on output interface to perform the morphological detection. After the morphological detection probe 500 detects a morphological detection echo signal, the morphological detection echo signal is transmitted to the morphological detection module 100 through the extended module 400 and the second interface 120 for processing. Where the extended module 400 may be an apparatus such as a hub that can divide one signal into a plurality of identical signals.

In one of the embodiments, the switch module is connected to M array elements in the compound probe, and is configured to control the M array elements to conduct with the elasticity detection module or the morphological detection module; and there are N array elements in the compound probe; where M is less than or equal to N; and M and N are positive integers.

Specifically, the compound probe may include 128 elements, when the elasticity detection or the morphological detection is performed, 16 elements may be selected for detection, 64 elements may also be selected for detection, or 128 elements may be simultaneously detected. A specific number of elements used may be adjusted according to an actual situation, which is not specifically limited in the present embodiment.

In one of the embodiments, the switch module includes a relay array.

The detection mode control circuit provided by an embodiment of the present disclosure includes a morphological detection module, an elasticity detection module and a switch module. The morphological detection module generates a morphological detection control signal according to a user instruction or a system setting, and transmits the morphological detection control signal to the switch module. The elasticity detection module generates an elasticity detection control signal and a second control signal according to the user instruction or the system setting, and transmits them to the switch module. The switch module selectively transmits the morphological detection control signal or the elasticity detection control signal to a compound probe according to control of the second control signal, and controls the compound probe to perform morphological detection or elasticity detection. Through the detection mode control circuit, the embodiment of the present disclosure controls the compound probe to perform morphological detection and elasticity detection, and use of the compound probe for detection enables an elasticity detection position to be more accurate, and further enables diagnosis data to be more accurate.

Preferably, the detection mode control circuit further includes an input module 700, where the input module 700 is connected to the morphological detection module 100 and the elasticity detection module 200, respectively, and configured to obtain input information from a user. The input module is further configured to generate the user instruction according to the input information from the user.

Specifically, the input module may be a smart phone (such as an android phone, an iphone operation system (iOS) phone, etc.), a tablet computer, a palmtop, a mobile Internet device (MID), a pad, a human machine interface (HMI), a computer, and other electronic devices that can perform data processing and human-computer interaction. The input module 700 is connected to the elasticity detection module 200 through a Universal Serial Bus (USB) interface, and the input module 700 is connected to the morphological detection module 100 through a peripheral component interconnect express (PCIE) interface.

Technical features of the above-mentioned embodiments may be arbitrarily combined. For the sake of brevity, not all possible combinations of the technical features of the above-mentioned embodiments are described. However, as long as there is no contradiction among the combinations of these technical features, they should be considered as the scope recited in the present specification.

The above-mentioned embodiments only show several implementations of the present disclosure, which are described specifically and in detail, but they should not be understood as limiting the scope of the patent for the present disclosure. It should be pointed out that for persons of ordinary skilled in the art, without departing from the concept of the present disclosure, several changes and improvements may be made, which are within the scope of protection of the present disclosure. Therefore, the scope of protection of the patent for the present disclosure should be subject to the appended claims.

What is claimed is:

1. A detection mode control circuit, comprising: a morphological detection module, an elasticity detection module and a switch module;
   wherein the morphological detection module is connected to the switch module and configured to generate a morphological detection control signal according to a user instruction or a system setting and transmit the morphological detection control signal to the switch module;
   the elasticity detection module is connected to the switch module and configured to generate an elasticity detection control signal and a second control signal according to the user instruction or the system setting, and transmit the elasticity detection control signal and the second control signal to the switch module; and
   the switch module is connected to a compound probe and configured to receive the morphological detection control signal, the elasticity detection control signal, and the second control signal, and transmit, according to the second control signal, the morphological detection control signal to the compound probe to perform morphological detection, or transmit, according to the second control signal, the elasticity detection control signal to the compound probe to perform elasticity detection.

2. The detection mode control circuit according to claim 1, wherein the morphological detection module comprises a first interface and a second interface, the morphological detection module is connected to the switch module through the first interface, and the morphological detection module is connected to a morphological detection probe through the second interface; the morphological detection module is configured to generate the morphological detection control signal and a first control signal according to the user instruction or the system setting; and the first control signal controls the first interface and the second interface to turn on or off, and transmits the morphological detection control signal to the switch module through the first interface, or transmits the morphological detection control signal to the morphological detection probe through the second interface to perform the morphological detection.

3. The detection mode control circuit according to claim 2, wherein the morphological detection module comprises a plurality of second interfaces.

4. The detection mode control circuit according to claim 2, wherein the detection mode control circuit further comprises an extended module, the extended module is connected to the morphological detection module through the second interface, and the extended module comprises a plurality of output interfaces which are respectively connected to the morphological detection probe.

5. The detection mode control circuit according to claim 4, wherein the morphological detection module is further configured to generate a third control signal according to the user instruction or the system setting, and transmit the third control signal to the extended module; and the extended module controls the plurality of output interfaces to turn on or off according to the third control signal.

6. The detection mode control circuit according to claim 5, wherein the third control signal controls each of the output interfaces of the extended module to turn on or off.

7. The detection mode control circuit according to claim 1, wherein the switch module is connected to M array elements in the compound probe, and is configured to control the M array elements to conduct with the elasticity detection module or the morphological detection module; and
   there are N array elements in the compound probe in total; wherein M is less than or equal to N, and M and N are positive integers.

8. The detection mode control circuit according to claim 7, wherein the switch module comprises a relay array.

9. The detection mode control circuit according to claim 1, wherein the detection mode control circuit further comprises: an input module; and
   the input module is respectively connected to the morphological detection module and the elasticity detection module, and is configured to acquire the user instruction or store system setting information.

10. The detection mode control circuit according to claim 9, wherein the input module is configured to obtain input information from a user and generate the user instruction according to the input information from the user.

* * * * *